United States Patent [19]

Löwenstein

[11] Patent Number: 5,291,900
[45] Date of Patent: Mar. 8, 1994

[54] INSTRUMENT FOR MEASURING THE LENGTH OF INFANTS

[76] Inventor: Dieter Löwenstein, Medizintechnik GmbH, 6501 Bodenheim, Fed. Rep. of Germany

[21] Appl. No.: 942,851

[22] Filed: Sep. 10, 1992

[30] Foreign Application Priority Data

Sep. 13, 1991 [DE] Fed. Rep. of Germany ... 9111428[U]

[51] Int. Cl.⁵ .............................................. A61B 5/103
[52] U.S. Cl. ..................................... 128/774; 33/773; 33/779
[58] Field of Search ................. 128/774, 781, 782; 33/772–775, 779–782

[56] References Cited

U.S. PATENT DOCUMENTS

| | | | |
|---|---|---|---|
| 4,383,301 | 5/1983 | Morita et al. | 33/772 |
| 4,472,881 | 9/1984 | Houck | 33/779 |
| 5,161,313 | 11/1992 | Rijlaarsadam | 33/773 |

FOREIGN PATENT DOCUMENTS 189160  12/1966  U.S.S.R. ............................ 33/141 R

Primary Examiner—Max Hindenburg
Attorney, Agent, or Firm—Michael D. Bednarek

[57] ABSTRACT

An instrument for measuring infants which include a housing that can be slid uniformly in a straight line on a base, a measuring device to record the translational motion, which is connected to a counter that displays the path traveled. The housing also can include a lamp device, in which an electrical light source is installed in such a way that it sends a beam of light, which is focussed, downward at a right angle to the direction of movement of the housing. The electrical light source thus creates a line-shaped light spot.

9 Claims, 2 Drawing Sheets

INSTRUMENT FOR MEASURING THE LENGTH OF INFANTS

FIELD OF THE INVENTION

The invention relates to an instrument for measuring the length of infants.

BACKGROUND OF THE INVENTION

According to the current state of the art, two persons are necessary to determine the length of an infant. The first person stretches the child out and the second person determines the length of the infant with a measuring tape.

Apart from the fact that two persons are always required for this measuring process, the measurement always presents a problem if the infant is in an incubator and every time the incubator is opened, it represents a significant stress for the child.

With the use of the measuring method described above, it is in fact unavoidable that the incubator has to be completely opened for measuring, since otherwise the measuring tape can not be laid out.

SUMMARY OF THE INVENTION

Thus the object of the invention is to create a simple device that makes it possible so that one person alone can reliably determine the length of an infant.

This object is achieved according to the invention with an instrument for measuring the length of infants, characterized by a housing (2) that can be moved uniformly in a straight line on a base (1), a device mounted in the housing (2) to emit a scanning beam (26) downward at a right angle to the base and a measuring device mounted in the housing to record and display a translational movement path between a starting point and a certain end point of a translational movement.

The device includes, in a housing that can be slid uniformly in a straight line on a base, a measuring device to record the translational motion, which is connected to a counter that displays the path traveled. The housing also includes a lamp device, in which an electrical light source is installed in such a way that it sends a beam of light, which is focussed, downward at a right angle to the direction of movement of the housing. The electrical light source thus creates a line-shaped light spot.

When we speak of a housing for the instrument in the sense of this description, this need not be a closed housing. It can also be a different frame construction, as long as it is suitable for holding the components of the instrument and for use as an instrument unit.

In a preferred embodiment, the housing is provided with running wheels for the translational movement, by means of which it can be slid on the base. In another preferred embodiment, an incremental rotary sensor is linked to the running wheels as a measuring device to record the translational movement.

Another preferred embodiment has a counter, which can be reset, to display the translational movement. The counter can be mechanically operated or set up as a digital counter. The counter displays the path that has been traveled uniformly in a straight line which is determined by the measuring device by means of a suitable circuit and/or measuring means and, in another advantageously constructed embodiment, also the direction that the path was traveled.

A construction of the instrument is also possible in which the housing includes a means for recording reflection signals of the scanning beam, which is also provided with a circuit that feeds the reflection signals into the measuring device that is present. Because of a first appropriate reflection signal, the display that can be reset is set to "zero," and the display (10) is stopped to store a final end dimension of the translational movement by a second suitable signal.

To the extent that no suitable base for operating the instrument is available, such a base can additionally be provided additionally as a frame with a runway such that the runway runs horizontally above the surface on which the infant lies and parallel to that surface.

The runway must generally be constructed such that it is transparent in the area of the light source.

The device according to the invention is constructed in an advantageous design so that it can be operated independently of the central power supply and is sized so that is not difficult to transport and, for example, can be also be used for house calls by midwives.

The device according to the invention, without linking a light beam sensor to the measuring device, is used in that the person performing the measurement stretches out the infant with one hand, and with the other hand, moves the device on the base that is arranged above the infant to the head or foot end of the infant and determines there the zero point of the measuring path and resets the counter to "zero." The device is then moved by hand on the base and to the other end of the infant's body, until the light beam just reaches the other end of the body. In this position, the path traveled, which corresponds to the body length of the infant, can be read on the counter. This measuring device makes it possible to measure infants, which for example are in an incubator, without the incubator needing to be completely opened because the person performing the measurement can stretch the child out straight through an opening that is present in the incubator and with the other hand slide the housing, with the measuring and counting device that is located in it, on the upper side of the incubator, which is usually transparent, e.g. made of PLEXIGLASS TM, and thus determine the body size of the infant.

BRIEF DESCRIPTION OF THE DRAWINGS

A preferred embodiment of the invention is shown in the drawings in which.

DETAILED DESCRIPTION

Figure 1:
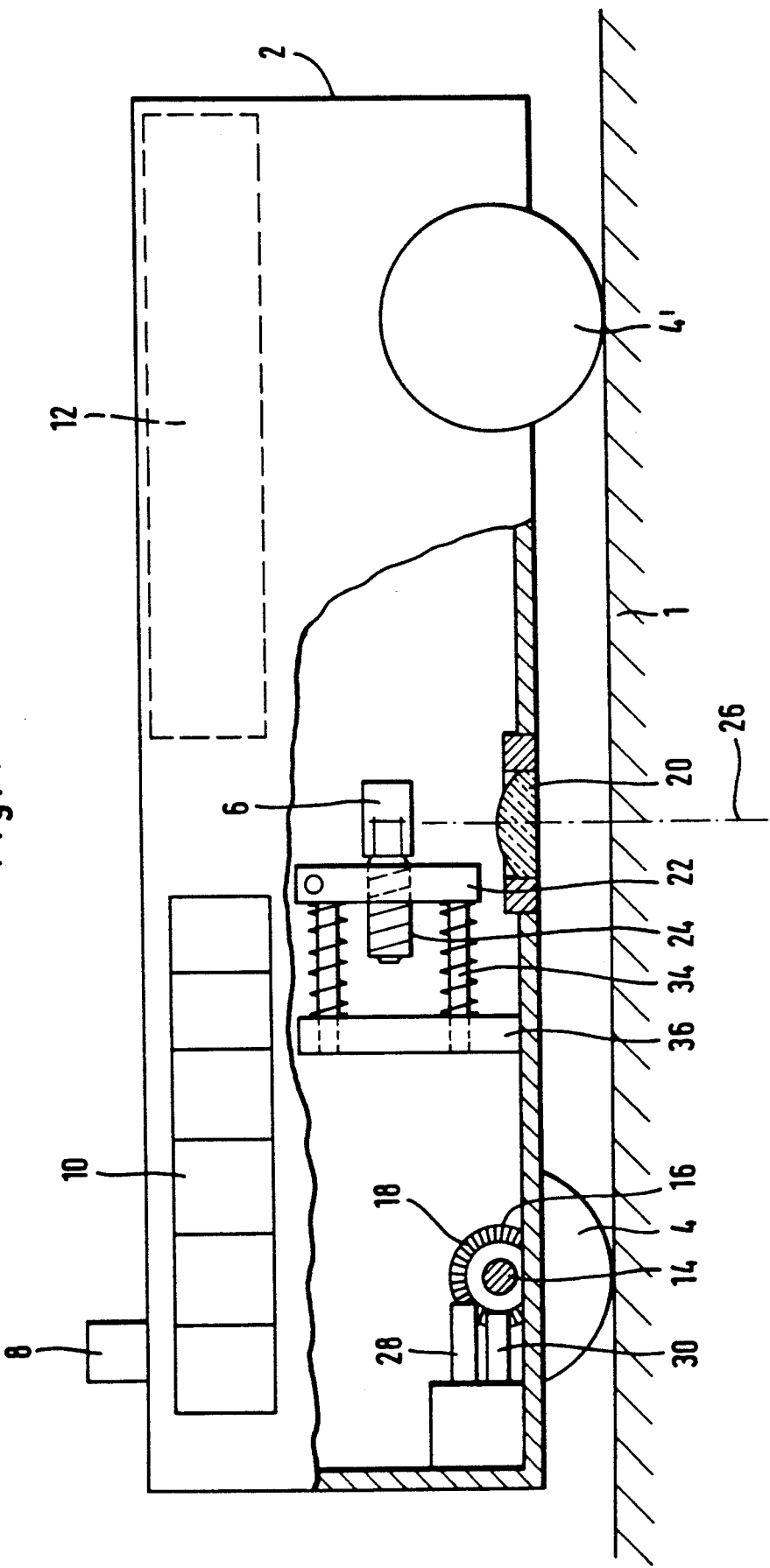
FIG. 1 a view of the device according to the invention.

FIG. 1 shows, on a base 1, a housing 2, on which running wheels 4, 4' are mounted, which are connected to an incremental rotary sensor 16. The rotary sensor is connected via a circuit and evaluation means (now shown) to a counter 10 that can be read from the outside, which can be reset to "zero" by means of a push button 8.

The incremental rotary sensor 16 is mounted on the axle 14 so that it can not move. Since the diameter of the disk 16 is smaller than that of the running wheels 4, 4', it is located completely on the inside of the housing 2 (see FIG. 2). On the incremental rotary sensor disk 16, marks 18 are present in uniform spacing, the total number of which has a defined ratio to the circumference of the running wheels 4, 4'. In this way, length units can be counted by turning the running wheels 4, 4'. The selection of length unit is made by changing the number of lines on the incremental rotary sensor disk 16.

A fork shaped photoelectric barrier 28, the light beam of which is interrupted by the locating marks on the disk, converts the revolution of running wheels 4, 4' into electrical square wave signals which are counted and displayed.

A second fork shaped photoelectric barrier 30 makes possible the recognition of rotational direction, in that shutters are mounted and displaced such that the electrical square wave signals arrive, displaced by 90°, at the evaluating means (not shown) which controls the backward or forward counting of the counter 10.

In addition, a light source 6 operated by battery 12 is mounted in the housing. The light source can be switched on and off by a switching device that is not shown here. The light source 6 radiates downward, perpendicular to the base 1 of the housing 2, whereby the light beam 26 is focussed. During this process, the electrical light source 6 creates a line shaped light spot that develops because of the fact that the lamp helix is formed by a plane convex lens 20 that is fastened in the base of the housing.

The person performing the measurement can determine, by means of the light beam 26 that is emitted straight downward, whether the instrument is in the correct "zero" position, in which the counter 10 is to be reset to "zero," in order to obtain a correct measurement of the body length of the infant. After resetting the counter 10 at one end of the infant's body, the housing is moved by hand uniformly in a straight line on the base to the other end of the infant's body. Reaching the other end of the body can in turn be determined by means of the light beam 26 emitted downward from the light source 6.

Figure 2:
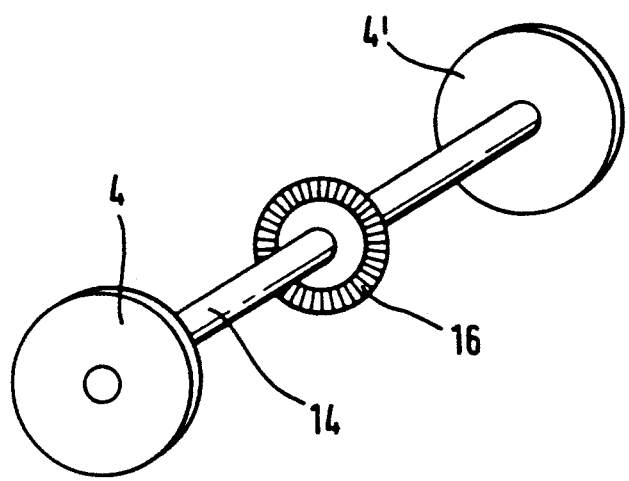
FIG. 2 a view of the incremental rotary sensor that is connected to the running wheels.

In FIG. 2, a preferred embodiment of the measuring device for determining the translational path travelled is pictured. Between the running wheels 4 and 4' that are connected by a rigid axle 14, an incremental rotary sensor 16 is mounted on rigid axle 14. The axle is mounted in the housing 2. The diameter of the disk of incremental rotary sensor 16 is smaller than the diameter of the running wheels 4 and 4', as a result of which it is located completely inside housing 2. On the incremental rotary disk 16, locating marks 18 are placed in equal spacing, the number of which has a defined relationship to the circumference of the running wheels. In this way, the length units that are traveled can be counted by turning the running wheels. The selection of length unit is made by an appropriate arrangement of locating marks 18 on the incremental rotary disk.

Figure 3:
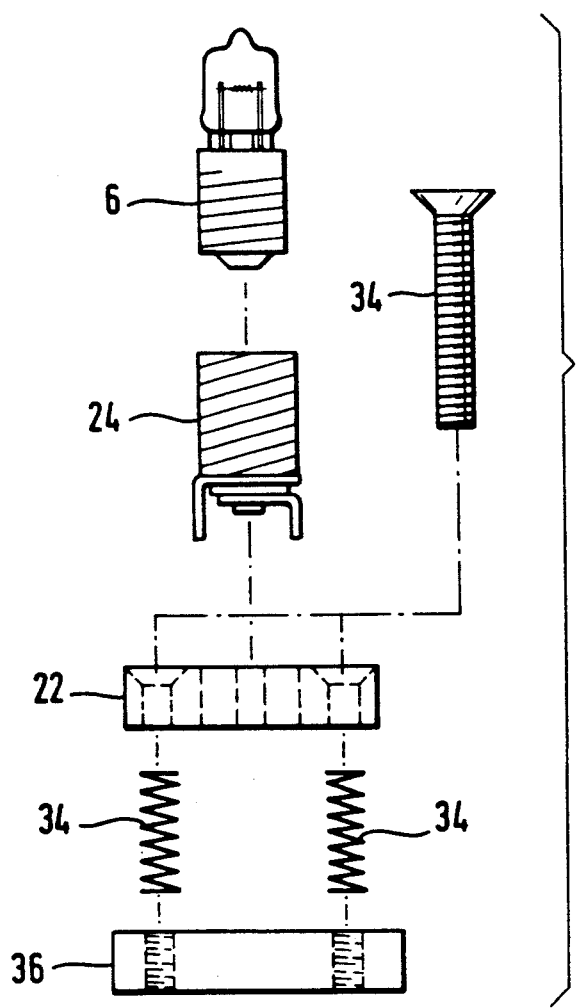
FIG. 3 an illustration of the light source with the mounting arrangement that goes with it.
Figure 4:
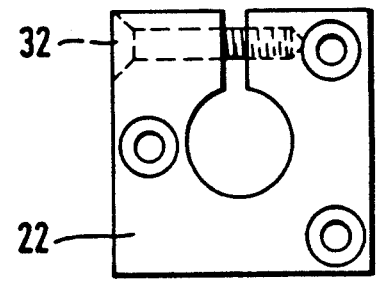
FIG. 4 is a top view of the slotted adjustable plate of the light source used in FIG. 3.

FIG. 3 shows in detail the electrical light source 6 and its fastening arrangement.

In order to compensate for manufacturing tolerances, it must be possible to adjust the lamp in three dimensions so that it can be moved radially with respect to the adjustable plate.

The slotted adjustable plate 22 is used as a bracket and for radial adjustment of the lamp socket 24, which the lamp 6 is screwed into. The fastening of the lamp 6 is by means of the clamping screw 32 shown in FIG. 3. The adjustable plate 22 can be adjusted three-dimensionally via three screwed pressure springs 34 connected to a base plate 36. The base plate 36 is mounted in housing 2.

I claim:

1. An instrument for use in conjunction with a base for measuring the length of infants, the instrument comprising:
    a housing that can be moved uniformly in a straight line on the base;
    a measuring device mounted in the housing for recording and displaying a translational movement path between a starting point and a certain end point of a translation movement; and
    a device mounted in the housing emitting a scanning beam downward at a right angle to the base, separate and offset from the measuring device.

2. An instrument according to claim 1, wherein the device for emitting a scanning beam comprises an electrical light source and beam focussing optics.

3. An instrument according to claim 1, wherein the housing includes a plurality of running wheels for translational movement on the base.

4. An instrument according to claim 3, wherein the measuring device for recording the translational movement comprises a digital rotary angle increment sensor that is mounted on one of the running wheels.

5. An instrument according to claim 4, wherein the display of the measuring device is an electronic digital display and wherein the rotary angle increment sensor emits signals and the measuring device is equipped with converting means for converting the signals of the digital rotary angle increment sensor into a length dimension on the display.

6. An instrument according to claim 5, wherein the converting means record the running direction of the running wheels and this information to the display device.

7. An instrument according to claim 1, wherein the measuring device comprises a display equipped with means to set the display to zero.

8. An instrument according to claim 1, further comprising means to record a reflection signal of the scanning beam mounted in the housing and a circuit to feed the reflection signal to the measuring device such that the display is responsive to first and second reflection signals fed to the measuring device so that the display is set to zero by the first reflection signal and the display is stopped to store a final end dimension of the translational movement by the second reflection signal.

9. An instrument according to claim 1, further comprising a frame having a runway which serves as the base for the translational movement, the frame being adapted for positioning over a horizontal working surface such that the runway runs horizontally above and parallel to the working surface.

* * * * *